(12) United States Patent
Melchior et al.

(10) Patent No.: US 7,060,292 B2
(45) Date of Patent: Jun. 13, 2006

(54) LIPID STRUCTURES AND USES THEREOF

(75) Inventors: Donald L. Melchior, Framingham, MA (US); Anthony Carruthers, Sutton, MA (US)

(73) Assignee: GESynthesis, Inc., Worcester, MA (US)

( * ) Notice: Subject to any disclaimer, the term of this patent is extended or adjusted under 35 U.S.C. 154(b) by 314 days.

(21) Appl. No.: 10/165,501

(22) Filed: Jun. 7, 2002

(65) Prior Publication Data

US 2003/0022154 A1 Jan. 30, 2003

Related U.S. Application Data

(60) Provisional application No. 60/296,904, filed on Jun. 9, 2001.

(51) Int. Cl.
*A61K 9/127* (2006.01)

(52) U.S. Cl. .................... 424/450; 424/1.11; 424/1.21; 436/63; 436/172; 435/317.1

(58) Field of Classification Search ............... 436/71, 436/63, 800; 435/4, 317.1, 455, 458, 325; 424/1.21

See application file for complete search history.

(56) References Cited

U.S. PATENT DOCUMENTS

| | | | |
|---|---|---|---|
| 5,094,819 A | 3/1992 | Yager et al. | |
| 5,106,610 A | 4/1992 | Harris et al. | |
| 5,709,994 A | 1/1998 | Pease et al. | |
| 6,063,589 A | 5/2000 | Kellogg et al. | |
| 6,107,066 A | 8/2000 | Tsien et al. | |
| 6,235,535 B1 | 5/2001 | Keinanen et al. | |
| 6,251,581 B1 | 6/2001 | Ullman et al. | |
| 6,302,134 B1 | 10/2001 | Kellogg et al. | |
| 6,342,379 B1 | 1/2002 | Tsien et al. | |

FOREIGN PATENT DOCUMENTS

WO    WO 98/37920    *  2/1998

OTHER PUBLICATIONS

Alberts et al "Molecular Biology of the Cell" 1994, Garland Publishing, Inc, 3rd Edition, pp. 480-483.*
Carruthers et al, Biochemistry, 1984, vol. 23, pp. 6901-6911.*
Barton et al. "Drug-Phospholipid Interactions. 2. Predicting the Sites of Drug Distribution Using *n*-Octanol/Water and Membrane/Water Distribution Coefficients" *J. Pharm. Sci.* 86: 1034-1039 (1997).

(Continued)

*Primary Examiner*—Leon B. Lankford, Jr.
*Assistant Examiner*—Allison M. Ford
(74) *Attorney, Agent, or Firm*—Clark & Elbing LLP; K. Bieker-Brady (57) ABSTRACT

This invention features in vitro methods of determining the rate and extent to which test compounds, such as drug candidates, enter, move within, and traverse lipid-associated barriers. This invention also features method that measure the accumulation, that is the partition coefficient, of test compounds in lipid structures relative to, e.g., an aqueous phase, as well as the rate of accumulation of test compounds in the lipid structures. In addition, the invention features lipid vesicles that contain fluorophores localized within the aqueous interior that can be employed in the methods described herein.

23 Claims, 8 Drawing Sheets

OTHER PUBLICATIONS

Carruthers et al. "A Rapid Method of Reconstituting Human Erythrocyte Sugar Transport Proteins" *Biochemistry* 23: 2712-2718 (1984).

Fix et al. "The Fluorosome™ Technique for Investigating Membrane On- and Off-Loading of Drugs by β-CD and Sonicated SUV" *FEBS Lett.* 516: 109-112 (2002).

Gobas et al. "A Novel Method for Measuring Membrane-Water Partition Coefficients of Hydrophobic Organic Chemicals: Comparison with 1-Octanol-Water Partitioning" *J. Pharm. Sci.* 77: 265-272 (1988).

Hsu et al. "Fatty Acid Transfer from Liver and Intestinal Fatty Acid-binding Proteins to Membranes Occurs by Different Mechanisms" *J. Biol. Chem.* 271:13317-13323 (1996).

Kansy et al. "Physicochemical High Throughput Screening: Parallel Artificial Membrane Permeation Assay in the Description of Passive Absorption Processes" *J. Med. Chem.* 41: 1007-1010 (1998).

Levine et al. "Structural and Physiologic Determinants of Human Erythrocyte Sugar Transport Regulation by Adenosine Triphosphate" *Biochemistry* 37: 12221-12232 (1998).

Melchior et al. "Application of Fluorosome Stopped-Flow Spectrophotometry to Monitor the Entry of Molecules into Lipid Bilayers" *Biotechnol. Tech.* 11: 885-888 (1997).

Melchior "A Rapid Empirical Method for Measuring Membrane Bilayer Entry Equilibration of Molecules" *J. Pharm. Sci.* 91: 1075-1079 (2002).

Noy, et al. "Kinetic Parameters of the Interactions of Retinol with Lipid Bilayers" *Biochemistry* 29: 3883-3888 (1990).

Ottiger et al. "Partition Behaviour of Acids and Bases in a Phosphatidylcholine Liposome-Buffer Equilibrium Dialysis System" *Eur. J. Pharm. Sci.* 5: 223-231 (1997).

Pauletti et al. "Partition Coefficients in vitro: Artificial Membranes as a Standardized Distribution Model" *Eur. J. Pharm. Sci.* 1: 273-282 (1994).

Sarmento et al. "Partition of Dopamine Antagonists into Synthetic Lipid Bilayers: The Effect of Membrane Structure and Composition" *J. Pharm. Pharmacol.* 45: 601-605 (1993).

Verkman "The Quenching of an Intramembrane Fluorescent Probe. A Method to Study the Binding and Permeation of Phloretin through Bilayers" *Biochim. Biophys. Acta* 599: 370-379 (1980).

* cited by examiner

LIPID STRUCTURES AND USES THEREOF

CROSS-REFERENCE TO RELATED APPLICATIONS

This application claims benefit of co-pending U.S. Provisional Application No. 60/296,904, filed Jun. 9, 2001.

BACKGROUND OF THE INVENTION

The invention relates to the fields of vesicles and molecular transport.

The advent of combinatorial chemistry and high-throughput screening allows the identification of many compounds as potential candidate drugs for therapeutic uses. Many potentially valuable drugs, however, are ineffective because they cannot traverse lipid-based barriers, such as cell membranes or intestinal, blood-brain, or placental barriers, or they cannot accumulate at the desirable side of such barriers in concentrations sufficient for therapeutic efficacy.

A drug selection process is needed that detects the physicochemical and pharmacokinetic characteristics of the test compound, i.e., factors that govern the ability of the compound to accumulate in the appropriate compartment. Preferably, such a selection process can be done at an early stage in the drug development process since failure to consider any of these characteristics can lead to significant and costly development problems, delays in getting the product to market, and the failure of the project altogether. This situation is exacerbated by strong pressure for rapid selection of the best candidate drugs for development.

Existing experimental methods for determining the rate and extent at which drugs and similar molecules penetrate physiological barriers are limited, inaccurate, slow, awkward and costly, and they are unsuitable for high throughput screening. Animal models are costly, controversial, labor intensive, and not suited to high-throughput screening. Simple cell culture models and cultured brain capillary endothelial cell and astrocyte models, while in many ways superior to the use of animals, also have various disadvantages, including variability of results and the need for sterile conditions. In addition, the utility of animal models and other in vitro model systems using cells or tissues is often compound-dependent, i.e., they typically require either the use of radioactively labeled test compounds or a spectroscopic detection method whose sensitivity depends on the chromophoric properties of the compounds. The use of radioactively labeled test compounds can introduce further complications resulting from related disposal requirements. These methods can be expensive and time consuming, and are rarely suitable for high-throughput screening programs. Additionally, there is the considerable time and expense of start-up and maintenance of the cell cultures. Although several artificial membrane models have been developed, they also suffer from limitations such as requiring fluorescent test compounds or not employing true lipid bilayers.

Although the rates of penetration of molecules into and through a membrane are ultimately determined by the structural features of the molecules, at present there is no reliable a priori theoretical means to calculate these rates for compounds that are predictive, e.g., for a potential drug, or for more complicated situations where the drug is deposited in a natural carrier molecule, such as serum albumin, or in a synthetic drug delivery vehicle. Thus, there is a need for new compositions and methods for measuring the transport of molecules through lipid barriers.

SUMMARY OF THE INVENTION

The invention features vesicle compositions and methods of use thereof. The vesicles contain a fluorescent molecule, whose fluorescence intensity is dependent on the presence (or absence) of a test compound. In the methods of the present invention, the fluorescence intensity of a fluorescent molecule associated with a lipid structure, e.g., a vesicle, is monitored as a function of time after the addition or removal of a test compound to the assay. By measuring the change in fluorescence as a function of time, the transport properties of a test compound into, out of, within, or through a lipid structure can be determined.

Accordingly, in one aspect, the invention features a vesicle including a lipid bilayer and a fluorescent molecule including a fluorophore bound to a carrier and disposed in the interior of the vesicle, wherein the carrier prevents the fluorophore from traversing the lipid bilayer. In various embodiments, the vesicle is not a biological cell. Exemplary fluorophores include 1,6-diphenylhexa-1,3,5-triene, nitrobenzene-2-oxa-1,3-diazole, tryptophan, tyrosine, dansyl chloride, pyrene, naphthalene, fluorescein, and derivatives thereof. In various embodiments, the carrier is a protein, a polypeptide, a sugar, a synthetic or natural polymer, or an emulsion. The fluorescent molecule may be a serum albumin or a serum lipoprotein. Exemplary lipid bilayers include a phospholipid (e.g., a phosphatidylcholine), sphingolipid, glycolipid, or analog thereof. Lipid bilayers may also include cholesterol, a protein, or derivatives thereof. In desirable embodiments, the lipid bilayer includes a cell membrane, for example, a bacterial, protozoan, animal (e.g., mammalian, such as intestinal endothelial), plant, fungal, or mycoplasma cell membrane.

In another aspect, the invention features a method of fabricating a vesicle (e.g., as described above) containing a fluorescent molecule. The method includes the steps of combining a lipid, an aqueous solution, and a fluorescent molecule comprising a fluorophore bound to a carrier to produce an aqueous suspension; and forming the vesicle from the aqueous suspension, wherein the vesicle includes a lipid bilayer, and the fluorescent molecule is disposed in the interior of the vesicle. In various embodiments, forming the vesicle includes agitating the aqueous suspension and passing the agitated aqueous suspension through a filter at least once (e.g., at least 21 times). In desirable embodiments, the filter has a pore size of greater than 10 nm and smaller than 1000 nm. In alternative embodiments, forming the vesicle includes employing sonication, solvent-injection, detergent dialysis, reverse-phase evaporation, hydration from a dry film, or French press extrusion.

The invention further features a method for characterizing a lipid transport property of a test compound. The method includes the steps of providing an aqueous suspension include a vesicle (e.g., as described above), which includes a lipid bilayer and a fluorophore; contacting the test compound with the aqueous suspension; and measuring a change in fluorescence of the fluorophore as a function of time. In desirable embodiments, the fluorophore is bound to a carrier and is disposed in the interior of the vesicle, wherein the carrier prevents the fluorophore from traversing the lipid bilayer; or the lipid transport property is the lipid-water permeability coefficient of the test compound. In other embodiments, the fluorophore is disposed in the lipid bilayer, e.g., the fluorophore is bound to a lipid in the lipid bilayer.

In another aspect, the invention features a method for characterizing a lipid-water partition coefficient of a test compound. The method includes the steps of providing a first aqueous suspension comprising a vesicle (e.g., as described above), which includes a lipid bilayer and a fluorophore; contacting the test compound with the first aqueous suspension; measuring a change in fluorescence of the fluorophore in the first suspension as a function of time; providing a second aqueous suspension including the vesicle, wherein the second aqueous suspension contains a different concentration of the vesicle than the first aqueous suspension; contacting the test compound with the second aqueous suspension; and measuring a change in fluorescence of the fluorophore in the second aqueous suspension as a function of time.

The invention also features an apparatus for determining a lipid transport property of a test compound. The apparatus includes an aqueous suspension of vesicles including a lipid bilayer and a fluorophore bound to a carrier and disposed in the interior of the vesicle (e.g., as described above); and a fluorescence detector. In various embodiments, the vesicle is not a biological cell. In other embodiments, the detector is capable of measuring fluorescence as a function of time. The apparatus may also include a device capable of contacting the test compound with the aqueous suspension, e.g., a high-throughput device. Exemplary high-throughput devices include a centripetal microfluidic device and a multi-well device. In various embodiments, the lipid transport property is the lipid-water permeability coefficient or the lipid-water partition coefficient. The apparatus may also include a computational device for determining the lipid transport property.

By "analog" is meant a chemical compound that is structurally similar to another but differs slightly in composition (as in the replacement of one atom by an atom of a different element or in the presence of a particular functional group). For example, the ester linkages in phosphoglycerides (or other lipids) may be replaced by ether linkages in a lipid analog. Analogs may be synthetic or naturally occurring.

By "biological cell" is meant a small usually microscopic mass of protoplasm bounded externally by a semipermeable membrane, usually including one or more nuclei and various other organelles with their products, capable alone or interacting with other cells of performing all the fundamental functions of life, and forming the smallest structural unit of living matter capable of functioning independently.

By "bound to" is meant attached via a chemical bond or other strong interaction, e.g., an electrostatic interaction, such that for two chemical species bound together, the two species do not dissociate (<1% dissociation) under experimental conditions.

By "carrier" is meant a usually inactive accessory substance, e.g., a molecule or aggregate, that may be used to render a compound soluble or suspendable in a particular medium, e.g., aqueous solution or lipid phase.

By "derivative" is meant a structural derivative having a chemical modification. Typically derivatives may be synthesized that increase or decrease solubility or alter another property of a compound. The term "derivative" also encompasses compounds that have been labeled with a probe molecule, e.g., a fluorophore.

By "diffusion coefficient $(D_m)$" is meant a measure of the rate of movement of a test compound in a given medium (e.g., water, lipid, or lipid bilayer).

By "disposed in the interior" of a lipid structure, e.g., a vesicle is meant located in a non-lipid phase, e.g., an aqueous solution, that is wholly enclosed by one or more lipid leaflets. For example, a lipid vesicle typically has a lipid bilayer surrounding an aqueous interior.

By "entry constant $(k_f)$" is meant a constant proportional to the rate at which a test compound penetrates a lipid layer, e.g., a bilayer.

By "equilibrium" is meant an experimental condition when concentrations of test compounds in all compartments (e.g., lipid bilayer, lipid vesicle internal water compartment, and extravesicular compartment) have stabilized (i.e., are invariant with time).

By "exit constant $(k_r)$" is meant a constant proportional to the rate at which a test compound passes out of a lipid layer, e.g., a bilayer.

By "FLUOROSOME®" is meant a lipoidal particle containing a probe molecule whose fluorescent properties change in the presence of a test compound.

By "fluorescent molecule" is meant a fluorescent chemical species. A fluorescent molecule may or may not be ionized in aqueous solution, and it may or may not be non-covalently associated with another chemical species or aggregate.

By "interior of a vesicle" is meant the non-lipid phase entrapped within the vesicle. Typically, the interior is an aqueous solution.

By "lipid analog" is meant a molecule that contains a lipoidal component, which is analogous in structure to naturally occurring lipids or analogous in physical properties, i.e., being amphipathic or primarily hydrophobic in nature.

By "lipid structure" is meant a physical form of lipids, including, e.g., a lipid bilayer, a micelle, lipid structures formed from a hexagonal lipid phase, a lipid monolayer, the cubic lipid phase, and an emulsion.

By "lipid bilayer" is meant a lipid structure composed of two lipid leaflets, being arranged so that the hydrophobic portion of the two leaflets are adjacent to one another, with their hydrophilic portions directed outward to form the opposing surfaces of the structure.

By "lipid leaflet" is meant a two dimensional array of lipid molecules, one molecule thick, (i.e., a monolayer).

By "lipid lamellae" is meant several lipid bilayers existing adjacent to one another or contained within a vesicle formed by another bilayer.

By "lipid phase" is meant the lipid portion of a lipid structure.

By "lipid transport property" is meant a measure of the ability of a compound to diffuse within, into, and/or out of a lipid structure. Exemplary lipid transport properties for a compound include the lipid-water permeability coefficient, the lipid-water partition coefficient, the lipid entry rate constant, the lipid exit rate constant, and the lipid diffusion coefficient.

By "lipid vesicle" is meant a particle consisting of an enclosed volume defined by a lipid bilayer.

By "membrane" is meant a lipid bilayer including within it proteins, carbohydrates, and/or other non-lipid molecules. Exemplary membranes include the barriers around biological cells, organelles within the cell, and other physiological structures. The term may also be used to refer to non-biological semi-permeable structures, e.g., a dialysis membrane.

By "membrane vesicle" is meant a particle consisting of an enclosed volume defined by a membrane.

By "micelle" is meant a globular lipid structure, in which the hydrophilic groups are disposed on the exterior surface and the hydrophobic groups are located within the interior.

By "microfluidic device" is meant a device having one or more fluidic channels that have cross-sectional dimensions of <1 mm, e.g., 500 µm, 300 µm, 100 µm, or smaller. A "centripetal microfluidic device" is a microfluidic device that uses centripetal forces to transport fluids.

By "molar flux (v)" is meant the amount of a test compound that passes across a unit area, e.g., of lipid bilayer or membrane, per unit time.

By "multilamellar vesicle" is meant a lipid vesicle containing more than one bilayer.

By "multi-well device" is meant a device having multiple wells, e.g., 96 or 384, for holding a plurality of fluid volumes. Each individual well is typically not fluidically connected to any other well.

By "partition coefficient (K)" is meant a constant describing the ratio of concentration of test compound in one state relative to a reference state at equilibrium, e.g., the amount in a membrane or lipid bilayer relative to that in the surrounding aqueous medium.

By "permeability coefficient (P)" is meant a constant proportional to the rate at which a specific test compound can cross a barrier, e.g., a lipid bilayer or membrane.

By "test compound" is meant a substance to be assayed for its lipid transports properties. Exemplary test compounds include drugs, drug candidates, metabolites, hormones, neurotransmitters, toxins, insecticides, and herbicides, either in solution or associated with a carrier, e.g., carrier proteins, carbohydrate aggregates, polymers, lipoidal structures, serum lipoproteins, or drug delivery vehicles.

By "unilamellar vesicle" is meant a lipid vesicle formed from a single lipid bilayer.

The methods described herein have several advantages over the methods of the prior art. The methods are applicable to a wide variety of test compounds, require only micromolar concentrations of test compounds, and measure entry rates with half-lives from milliseconds to hours. In addition, the methods do not employ animals or living cells, do not require sterile conditions, and do not require radiolabels. The methods are also amenable to robotics and suitable for high-throughput screening. In addition, vesicles containing fluorophore in the interior allow for the direct measurement of a test compound traversing a lipid layer.

Other advantages and features will be apparent from the following description and the claims.

BRIEF DESCRIPTION OF THE DRAWINGS

FIG. 1A depicts a vesicle before a test compound has traversed the lipid bilayer. FIG. 1B depicts a vesicle after a test compound has traversed the lipid bilayer. In FIG. 1B, the signal out is attenuated or increased in response to the presence of the test compound.

DETAILED DESCRIPTION OF THE INVENTION

The invention features in vitro techniques suitable for the assaying of a test compound, such as a drug candidate, for lipid transport properties. The technique is based on the actual penetration of a compound into or through a lipid structure, e.g., a bilayer. This method is capable of measuring the properties of a test compound, both when that test compound is dissolved in an aqueous solution and when it is associated with a carrier. In addition, the invention features lipid vesicles containing fluorescent molecules that may be employed in the lipid transport assays described herein.

Lipid Structures

Lipid structures that can be used in the methods described herein include, without limitation, uni- or multilamellar vesicles, micelles, emulsions, and films. The type and composition of the structure employed will depend on the desired application. The lipid structures may be barriers between two compartments. For example, a lipid bilayer film may be used to separate two aqueous compartments, and a lipid vesicle may separate an aqueous interior from an external solution. Depending on the lipid and the lipid structure employed, compartments separated by the structures may contain aqueous solutions, other polar-solvent solutions, non-polar solvent solutions, gels, or solids.

Lipids. Any natural or synthetic lipid or lipid analog that forms a stable structure, e.g., a vesicle, may be used in a lipid structure of the invention. Exemplary lipids include phospholipids (e.g., phosphoglycerides), ether lipids (e.g., glyceryl ether phospholipids and plasmologens), sterols (e.g., cholesterol), steroids, glycolipids, sphingolipids, hopanoids, carotenoids, terpenoids, and other lipids from cell or organelle membranes. In one embodiment, the lipid structure is formed from isolated cell membranes, e.g., from bacteria, fungi, protozoa, plants, or animals (e.g., mammalian intestinal epithelial cells). In another embodiment, the lipid structures contain a phosphatidylcholine, e.g., from egg. Lipids that may be used in the present compositions and methods are commercially available or may be synthesized or isolated from natural sources by methods known in the art.

Other Components. In addition to lipids, a lipid structure of the invention may include other compounds, e.g., proteins, polypeptides, sugars, nucleic acids, synthetic or naturally occurring polymers, and small organic molecules (e.g., fatty acids, aromatic compounds, alcohols, and glycols), to reproduce general or specific processes facilitated or catalyzed by such substances, e.g., in physiological membranes. For example, membrane bound proteins, such as P-glycoprotein or other pumps, may be included in assays for drug entry into cells containing efflux pumps. These additional compounds are, for example, dispersed within the lipid phase, attached to the lipid phase as pendant groups, or within a compartment enclosed by the lipid phase, e.g., the interior of a vesicle.

Fluorophores. Any fluorescent molecule can be used in the invention, provided that it can be sequestered in the appropriate phase, e.g., inside a lipid leaflet or in the aqueous interior of a vesicle. Exemplary fluorescent molecules include 1,6-diphenylhexa-1,3,5-triene (DPH), nitrobenzene-2-oxa-1,3-diazole, tryptophan, tyrosine, BODIPY® dyes, fluorescein, tetramethylrhodamine, TEXAS RED®, pyrene, perylene, cis- and trans-parinaric acid, retinal, anthracene, dansyl chloride, proteins (e.g., serum albumins, serum lipoproteins, and other fluorescent proteins (such as green fluorescent protein and yellow fluorescent protein)), chemically or genetically altered proteins, synthetic polypeptides, natural or synthetic polymers containing fluorescent monomers, and derivatives thereof. Exemplary serum albumins include those of human, bovine, caprine, and ovine origin. Examples of serum lipoproteins include a chylomicron, chylomicron remnant, intermediate-density lipoprotein, very low-density lipoprotein, low-density lipoprotein, and high-density lipoprotein.

Fluorophores may be located within the lipid phase (e.g., within a lipid bilayer or micelle) or within an aqueous (or polar solvent or gel or solid) compartment defined by the lipid structure. Hydrophobic fluorophores or fluorophores bound to hydrophobic compounds (e.g., a lipid) are used to localize the fluorophore within the lipid phase. To localize a fluorophore in a hydrophilic compartment of a lipid structure, e.g., an aqueous interior of a vesicle, the fluorophore may be hydrophilic or bound to a hydrophilic compound, i.e., a water-soluble or water-suspendable carrier. Desirable carriers prevent the fluorophore from diffusing out of a lipid structure. The properties of the carrier that effect this localization include molecular weight, hydrogen bonding to water, and ionization. Exemplary carriers include proteins, polypeptides, synthetic or natural polymers (e.g., poly(ethylene glycol), poly(ethylene oxide), starch, cyclodextrin polymers, and water-soluble cellulose derivatives (e.g., hydroxypropyl cellulose), nucleic acids, and carbohydrates (e.g., cyclodextrin). When covalently bound, the fluorophore may be attached to the carrier by any suitable chemical reaction. In desirable embodiments, fluorophores are attached to carriers by ester or amide bonds. In an alternative embodiment, a fluorophore may be localized within a stabilized colloidal particle (e.g., as in an emulsion) that will not associate with another lipid phase, e.g., a vesicle bilayer. In addition, a hydrophobic fluorophore may be tethered to a carrier such that the fluorophore is within a lipid leaflet but localized near the surface. The fluorophore may also be a fluorescent side chain of an amino acid (e.g., tryptophan or tyrosine) that is part of a protein (e.g., a serum albumin); the remainder of the protein then acts as the carrier for the fluorophore.

Preparation of Lipid Structures

Lipid structures may be prepared by any method known in the art (Gennis, R. B. *Biomembranes: Molecular Structure and Function* Springer-Verlag: New York, 1989). The fluorophore can be included in the lipid before the structure is formed, included in the hydrating solvent during manufacture, or introduced into preformed structures by techniques such as injection from a solvent such as diethyl ether or dimethylsulfoxide (DMSO), fusion with fluorophore containing lipid vesicles, detergent dialysis, or electroporation. In desirable embodiments, e.g., for drug discovery or other cell-based applications, the lipid structures are vesicles. In other desirable embodiments, the vesicle is not a biological cell.

Preparation of Probe-containing Lipid Vesicles—FLUOROSOMES®

Probe contained in lipid bilayer. In one example, lipid vesicles may be manufactured by drying down a lipid, such as egg phosphatidylcholine, from a solution of the lipid in a solvent, e.g., chloroform, by using a stream of gas, e.g., $N_2$. The resulting film is placed under vacuum (about 100 µm Hg) for approximately 1 hour to remove residual solvent. The film is taken up in buffer and agitated to form multilamellar vesicles. Large unilamellar vesicles are formed by multiple passages of the multilamellar suspension through an extrusion device using filters, e.g., polycarbonate filters having a pore sizes of greater than 10, 50, 75, 100, 150, 250, 500, and 1000 nm and/or less than 1000, 500, 250, 150, 100, 75, 50 or 10 nm. An exemplary filter has an average pore size of about 100 nm (e.g., ±2.5 nm). Probe-containing lipid vesicles or FLUOROSOMES® are then formed by rapidly adding appropriate amounts of a fluorescent probe, such as DPH or NBD, dissolved in a dispersing solvent, e.g., N,N-dimethylformamide (DMF) or DMSO, into a vigorously stirred suspension of the unilamellar vesicles. The amount of dispersing solvent present during vesicle manufacture is less than 0.25% (v/v). The vesicles are then diluted to the desired concentration by the addition of buffer. Bilayer concentrations of fluorophore, e.g., DPH, typically used range from 0.005% to 10% (mol % fluorophore:lipid), e.g., 0.5%, 1%, or 5%.

Alternately, vesicles can be manufactured by initially adding the fluorophore to the starting solution of lipid, e.g., egg phosphatidylcholine, drying the resulting solution down, putting this film under vacuum, adding buffer, and subjecting the resultant suspension to the extrusion process. A variety of techniques other than pore extrusion may be used to form unilamellar vesicles from the suspension and are known in the art. These techniques include sonication, solvent-injection, detergent dialysis, reverse-phase evaporation, hydration from a dry film, or French press extrusion.

Probe contained in aqueous interior of lipid vesicles. In another example, hydrophilic fluorophores or the complex formed by a hydrophobic fluorophore, such as DPH, covalently bonded to or otherwise tightly associated with a carrier, such as a cyclodextrin or a protein, such as a serum albumin, are localized within a lipid-bound compartment, e.g., the interior, water-filled space of a lipid vesicle. The manufacture of lipid vesicles with the encapsulation of the fluorophore or fluorophore-carrier complex (typically at a concentration of 0.5–5 mol % of lipid) is typically carried out with the fluorophore added in aqueous suspension of a lipid and unilamellar vesicle formation employing methods, such as pore extrusion (Melchior J. Pharm. Sci. 2002 91:1075–1079), reverse phase evaporation, or detergent dialysis with freeze-thaw (Carruthers et al. Biochemistry 1983, 23:2712–2718; Levine et al. Biochemistry 1998, 37:12221–12232). Following fluorophore encapsulation, lipid vesicles are typically washed several times in fluorophore-free buffer to remove non-encapsulated material.

Methods for Measuring Lipid Transport Properties of Test Compounds

The methods of the invention are used to measure the lipid transport properties of a test compound. These properties can then be used to determine test compounds (or lipid structures) with desirable properties, e.g., bioavailability. The lipid transport properties measurable by the methods described herein include:

1. the permeability coefficient (P) of a test compound for its passage through a lipid structure, e.g., structures that mimic cell membranes, the intestinal endothelial lining, and barriers such as the blood-brain, cerebrospinal, or placental barrier;

2. the entry rate ($k_f$) of a test compound into and the exit rate ($k_r$) of a test compound out of a lipid structure;
3. the partition coefficient (K), i.e., the accumulation of a test compound into a lipid structure relative to the surrounding environment; and
4. the diffusion coefficient of a test compound within the lipid phase of a lipid structure.

Figure 1:
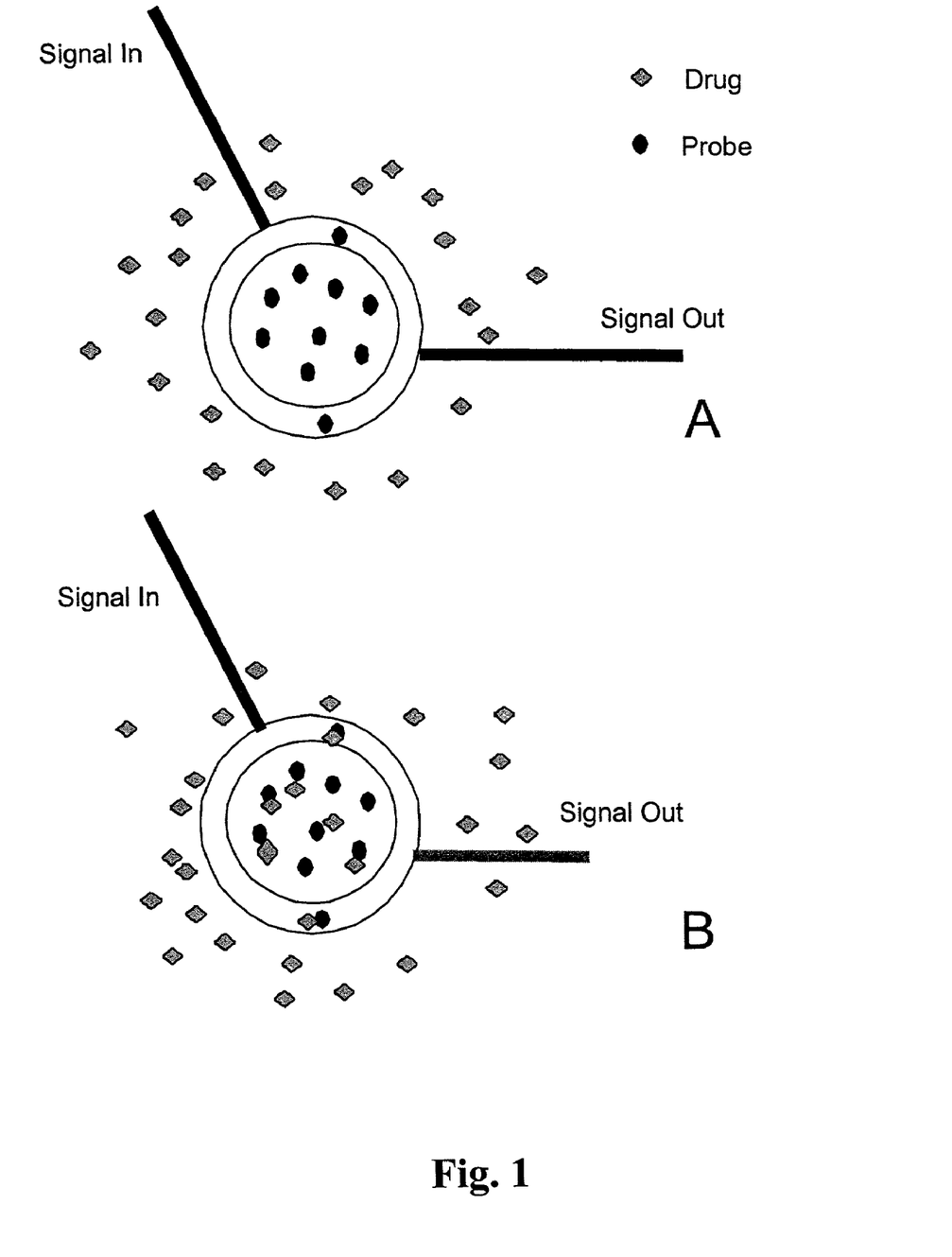
FIGS. 1A and 1B are schematic illustrations of vesicles of the invention.

Our methods typically employ an aqueous suspension of lipid structures, e.g., vesicles (FIG. 1). These structures, described above, typically range in size from approximately 25 nanometers to several micrometers, e.g., vesicles with ~100–150 nm diameter. In various embodiments, the lipid structures have a dimension larger than 25, 50, 100, 250, 500, 1000, or 10,000 nm and/or smaller than 10,000, 1000, 500, 250, 100, 50, or 25 nm. In an assay, a fluorophore emits fluorescence in response to excitation light (FIG. 1A). The magnitude of this fluorescence emitted by the fluorophore is altered by the presence of a test compound (FIG. 1B).

Measurements can be made by addition of a test compound to fluorophore-containing lipid structures, e.g., vesicles, addition of a test compound to a series of solutions containing different concentrations of fluorophore-containing lipid structures; addition of a fluorophore-containing lipid structure to a solution of test compound; and addition of a series of fluorophore-containing lipid structures of differing concentration to a solution of test compound. Other such combinations and permutations are readily apparent to one skilled in the art. Changes in fluorescence may be measured as a function of time or after equilibrium has been reached. The excitation wavelength employed and the emission wavelength monitored will depend on the fluorophore used. The temperature of the suspension may be regulated (e.g., kept constant) during an assay. Methods for regulating the temperature include, e.g., those employing a water bath, forced air, and heating tape.

The determination of lipid transport properties using the present methods depends on the kinetics of a test compound coming into contact with a fluorophore. Typically, this process is first order with respect to the test compound, i.e., for a given concentration of vesicle and fluorophore, the rate is proportional to the concentration of test compound. Other kinetic schemes are also possible.

Measurement of Movement of a Test Compound Across a Lipid Structure.

For these assays, a lipid structure, e.g., a vesicular bilayer, separates the fluorophore from the solution in which the test compound will be introduced. As the test compound passes through a lipid barrier, the fluorescence intensity of the fluorophore is altered over time. Measuring this change in fluorescence as a function of time allows for the determination of the ability of the test compound to cross the barrier.

Figure 2:
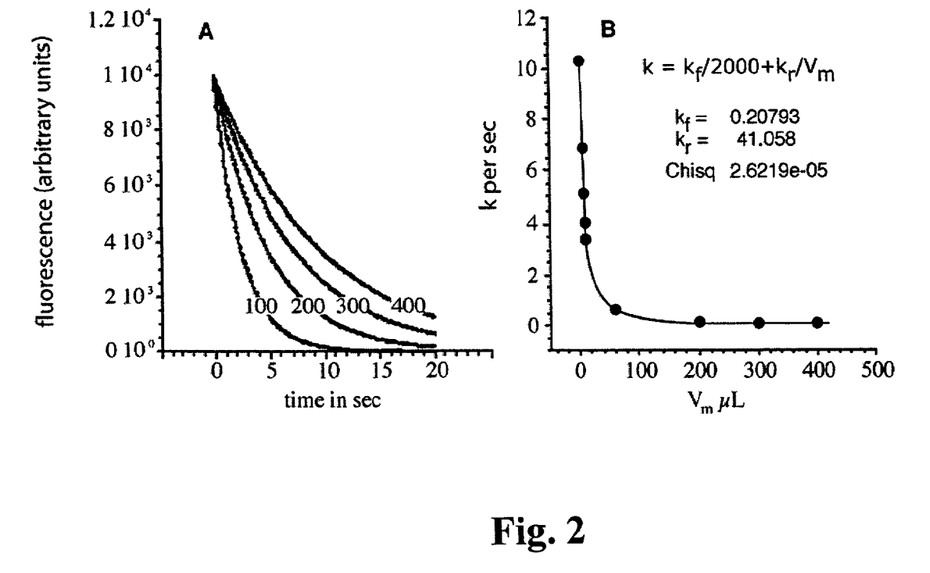
FIG. 2A is a graph of the change in fluorescence of DPH located within the lipid phase of an egg phosphatidylcholine vesicle as a function of time for various amounts of vesicles.
FIG. 2B is a graph of the rate constant for fluorescence change ($k_n$) as a function of lipid volume ($V_m$).

For example, lipid vesicles having fluorophores encapsulated within the aqueous interior are suspended in buffer; test compounds are injected into the lipid vesicle suspension; and the time course of test compound entry is monitored by fluorescence (FIG. 2). Test compound entry is revealed as an increase or as a decrease in fluorescence depending on the nature of the fluorophore and the test compound.

Calculation of permeability coefficient (P). The rate constant ($k_n$) and maximum extent of ($\Delta_m$) fluorescence change are determined using direct curve fitting procedures (nonlinear regression) assuming that test substance movement is a simple first order process. Deviation from first-order kinetics may be encountered when test compound movement into, out of, or across the membrane is carrier- or channel-mediated or the drug concentration approaches saturation. Occasionally the fluorescence signal is comprised of more than one exponential process, e.g., because of photobleaching of the fluorophore occurring simultaneously (Fix et al. FEBS Lett. 2002, 516:109–112). In general an increasing signal takes the form:

$$E_t = E_b + E_n(1 - e^{-k_n t}) + E_{n+1}(1 - e^{-k_{n+1} t}) + \ldots$$

and a decreasing signal takes the form:

$$E_t = E_b + E_n e^{-k_n t} + E_{n+1} e^{-k_{n+1} t} + \ldots,$$

where $E_t$ is the fluorescence of the system at time t, $E_n$ is the fluorescence of the system either at time zero (for a decreasing signal) or infinity (for an increasing signal), $E_b$ is the system fluorescence insensitive to addition or removal of test compound, t is time, and $k_n$ is the rate constant describing the rate of fluorescence decrease or increase. If more than one first order process is detected, the second or third processes are characterized by $E_{n+1}$, and $k_{n+1}$ and by $E_{n+2}$ and $k_{n+2}$, respectively.

The half-life for test compound movement across the bilayer is computed from the rate constant as $$t_{1/2} = 0.693 / k_n.$$

The molar flux (v) of a test compound across the membrane is computed as $$v = \frac{k_n [D]}{C_A} (\text{mol cm}^{-2} s^{-1}),$$

where [D] is the concentration of the test compound (M), and $C_A$ is the surface area presented by the lipid vesicles in solution ($cm^2$ per L water). Assuming lipid vesicles are spherical, $C_A = 3000/r$ $cm^2$ per L water where r is the radius of the vesicle in cm.

The permeability coefficient (P) for test compound movement across the membrane is computed as $$P = \frac{k_n}{C_A} (\text{cm} \cdot s^{-1}).$$

Measurement of the Entry and Exit Constants for a Test Compound

Entry and exit rates may be measured using lipid structures containing a fluorophore within the lipid phase. As a test compound enters or exits the lipid phase of the structure, the fluorescence intensity of the fluorophore is altered. Rate constants ($k_n$) for and maximum extent ($\Delta_m$) of fluorescence change are determined by analysis of the fluorescence decay curves assuming first order kinetics (see above). The assay is repeated using a fixed test compound concentration, [D], and varying concentrations of lipid vesicles.

Figure 4:
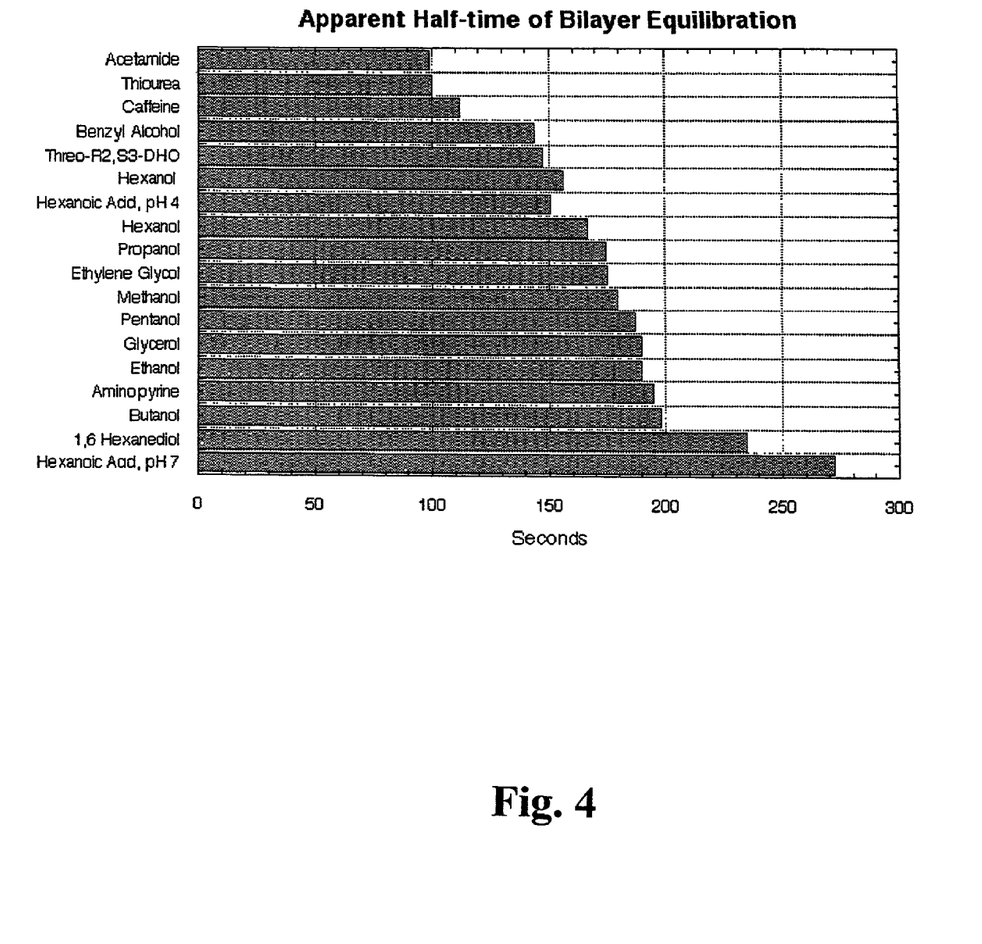
FIG. 4 is a graph of the half-lives for various compounds entering a lipid bilayer.

In one example, lipid vesicles are prepared that contain fluorophores within the lipid bilayer. The rate constant, $k_n$, describing test substance accumulation in the membrane is described by the following expression, derived from first principles:

$$k_n = \frac{k_f}{V_w} + \frac{k_r}{V_m},$$

where $k_f$ and $k_r$ refer to first order rate constants describing the rate of test compound movement from aqueous buffer (or other polar solvent) into the lipid bilayer (entry) and out of the lipid bilayer into the aqueous buffer (exit), respectively, $V_w$ and $V_m$ are the volumes (liter) of aqueous buffer and lipid bilayer present in the test vessel, respectively. $V_m$ is computed from the known partial specific volume of lipid bilayers formed from the lipid mixture under study (Melchior et al., Biochemistry 1980, 21:4828–4834) and from the amount of lipid in the vessel. Plotting $k_a$ versus $1/V_m$ results in a straight line with y-intercept=$k_f/V_w$ and slope $k_r$ (FIG. 4). Thus, analysis of the dependence of $k_n$ on $V_m$ permits direct computation of $k_f$ and $k_r$.

Calculation of the partition coefficient (K) of a test compound. The lipid-water partition coefficient (K) for the test compound, i.e., its accumulation by the lipid bilayer, can be determined from the relationship:

$$K = \frac{k_f}{k_r}.$$

Calculation of Test Compound Mobility within the Lipid Structure

The permeability coefficient P and the partition coefficient K can be used to calculate the mobility of a test substance (the diffusion coefficient $D_m$) within a lipid structure, e.g., within a bilayer, by:

$$D_m = \frac{P\lambda}{K}(\text{cm}^2 \cdot s^{-1}),$$

where $\lambda$ is the lipid structure thickness.

Apparatus

The methods of the invention include two basic steps: i) contacting a test compound with a lipid structure containing a fluorophore and ii) detecting fluorescence of the fluorophore as a function of time. The methods may also include a data analysis step to determine a lipid transport property of the test compound. These steps may be carried out manually or automatically using any equipment suitable for the task. For example, a computer-controlled pipettor may effect the introduction of a test compound to a suspension of vesicles. Exemplary devices for contacting the test compound with the lipid structure ensure that test compound is mixed as quickly as possible with the suspension of lipid structure to ensure accurate kinetic measurements. The data analysis of the change in fluorescence may be accomplished using appropriate software (e.g., KALEIDAGRAPH®, Synergy Software, Reading, Pa.) on a suitable computational device (e.g., a personal computer). Suitable devices for contacting the test compound with the lipid structure, fluorescence detection, and data analysis are known in the art.

High-throughput Methods

The methods of the invention are amenable to high-throughput screening. Exemplary high-throughput devices allow for at least 4, 8, 16, 32, 64, 96, or 384 assays. For example, individual test compounds or lipids or differing concentrations of test compounds or lipid structures may be tested in series or in parallel. In one embodiment, a multi-well device, such as a 96- or 384-well microtiter plate, is employed. In such a device, test compounds can be added serially or in parallel, e.g., using manual or computer-controlled pipettors. The fluorescence intensity can then be monitored for each well, sequentially or simultaneously. Such systems are known in the art.

In an alternative embodiment, a microfluidic device is employed. Such a device can be used to carry out numerous assays simultaneously (or in series). Exemplary microfluidic systems are disclosed in U.S. Pat. Nos. 6,063,589 and 6,302,134, hereby incorporated by reference. In these systems, centripetal forces are used to transport fluids through various channels. These systems may include mixers that are capable of rapidly mixing two solutions, e.g., a solution of test compound and a solution of lipid structure. The use of real-time fluorescence detectors with the device enables detection of the change in fluorescence of the test compound. Other suitable high-throughput devices are known in the art.

Applications

The lipid structures and methods of the invention can be used for a variety of applications. Exemplary applications include drug discovery (both for compounds that are active within a cell and those that are active extracellularly), environmental science, purification, extraction, decontamination, and development of chemical species such as herbicides and pesticides. The assays can test for desired properties of the test compound or the lipid structure. For example, the assays may be used to test lipid structures that are used to sequester chemical species from a solution, e.g., for decontamination or extraction.

Test Compounds

Any molecule or aggregate that is suitably stable (i.e., does not degrade during the experiment) in aqueous solutions (or other polar solvent solutions) may be used as a test compound in the methods described herein. The test compounds may be dissolved in solution, suspended in a dispersing agent such as DMSO, or associated with a carrier, such as a protein, sugar, carbohydrate aggregate, polymer, lipoidal structure, serum lipoprotein, or drug delivery vehicle. The test compound may also be attached to another molecule by an unstable chemical bond or as part of a degradable polymer as in biodegradable controlled release devices. The test compound may also be a mixture of compounds that act in combination with one another.

Alternative Embodiments

Although the above discussion focused on fluorophores, other types of probes, such as NMR, ESR, and phosphorescent probes, may be substituted for the fluorophore with an appropriate substitution of detector. In addition, the methods may be used for structures other than those containing lipids. For example, the methods may be used to determine transport properties in systems containing semi-permeable membranes (e.g., dialysis membranes), protein-based barriers, sugar-based barriers, or other natural or synthetic polymer barriers.

The following examples are merely to illustrate the invention are not intended to limit the invention in any way.

EXAMPLE 1

In a typical experiment, lipid vesicles were made from egg phosphatidylcholine with the fluorophore, e.g., DPH, located in the aqueous interior of the vesicle. These vesicles were suspended in 2 ml buffer and placed in a fluorimeter. The suspension was excited using light at 356 nm, and emission was measured at 428 nm. Test compounds typically at a concentration of 0.1 mM or less, which was well within the linear range for fluorophore quenching, were delivered by injection of 1 to 10 µl into the suspension (2.5 µl being the typical volume), and the time course of test substance entry was monitored. The time course was observed to result in an increase or a decrease in fluorescence depending on the nature of the probe and the test compound.

EXAMPLE 2

An example of a partition coefficient measurement made by our technique is shown in FIG. 2, which demonstrates the time course of entry of ethanol into a lipid bilayer, formed from egg phosphatidylcholine and containing DPH. In this experiment, 10 µl of ethanol was added to 2 ml of saline containing lipid vesicles having 100, 200, 300, or 400 µl of membrane bilayer at time zero. The volume of saline was held constant so that the instantaneous concentration of ethanol at time zero was also constant. The decrease in fluorescence with time reflects the entry of ethanol into the lipid bilayer.

The data of FIG. 2A were analyzed using the expression for a decaying signal (described above). Only a single exponential term was necessary to obtain a fit ($R^2 > 0.98$ in all instances), $E_b$ was zero, and $E_n$ was $1 \times 10^4$ in all instances (a consequence of the data collection procedure). The results were for 100 µl, $k_n = 0.41$ per second; 200 µl, $k_n = 0.20$ per second; 300 µl, $k_n = 0.14$ per second; 400 µl, $k_n = 0.10$ per second. A plot of $k_n$ vs. $V_m$ gave the curve of FIG. 2B, which after nonlinear regression, yielded $k_r = 41 \times 10^{-6}$ per second and $k_f = 2.1 \times 10^{-7}$ per second. Alternatively, $k_n$ can be plotted as a function of $1/V_m$, and $k_f$ and $k_r$ can be determined by linear regression. The partition coefficient, K, is $5.1 \times 10^{-3}$.

EXAMPLE 3

Figure 3:
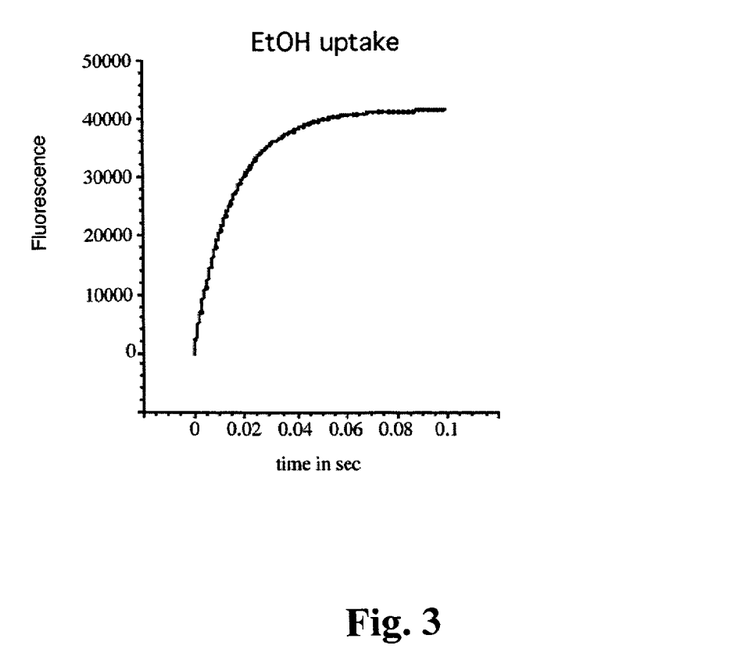
FIG. 3 is an inverted graph showing the rate of ethanol entry into the interior of a vesicle.

In this example, a lipid vesicle was formed from egg phosphatidylcholine with DPH covalently bonded (esterified) to cyclodextrin and contained in the aqueous interior of the vesicle. Upon addition of ethanol, the ethanol crosses the bilayer, penetrates the intravesicular water space, and quenches DPH fluorescence. FIG. 3 shows such an experiment (the DPH fluorescence was inverted to reflect the time course of ethanol uptake).

Ten µg of lipid vesicles loaded with cyclodextrin-esterified DPH (0.1–5 mM cyclodextrin) in 2 ml of buffer were mixed with 10 µl ethanol at time zero. The surface area presented by the lipid vesicles was approximately 25 cm². Fluorescence measurements were acquired, and the resulting curve was consistent with uptake as a single first order process. The resulting rate constant $k_n$ was 62.9 per second. This rate constant is used to compute the permeability P, resulting in $P = 5 \times 10^{-3}$ cm·s$^{-1}$. Knowing $K(5.1 \times 10^{-3})$ from Example 1 and assuming $\lambda = 40 \times 10^{-8}$ cm, $D_m$ is computed as $D_m = 3.9 \times 10^{-7}$ cm$^{-2}$·s$^{-1}$. These values compare with reported values of $K = 5.7 \times 10^{-3}$, $P = 2.1 \times 10^{-3}$ cm·s$^{-1}$ and $D^m = 1.5 \times 10^{-7}$ cm$^{-2}$s$^{-1}$ (Stein *Transport and Diffusion across Cell Membranes*, Academic Press: New York, 1985).

EXAMPLE 4

The experiment of Example 2 was repeated with several test compounds. The results are shown in FIG. 4. The half-lives are related to $k_n$, which in turn is related to the permeability coefficient. The results demonstrate the wide dynamic range of the measurements.

EXAMPLE 5

Vesicles were fabricated by first agitating a suspension of egg phosphatidylcholine in buffer (pH 7.0) to form multilamellar vesicles. Unilamellar vesicles were then formed by 21 passages of the multilamellar suspension in a LIPO-FAST® Extrusion Apparatus (Avestin Inc., Ottawa, Canada) using 100-nm polycarbonate filters (Melchior J. Pharm Sci. 2002, 91:1075–1079). A solution of the fluorophore in DMF was then added to a vigorously stirred suspension of the unilamellar vesicles. The vesicle size was 149 nm, as determined by photon correlation photometry. The excitation wavelength was 356 nm, and fluorescence was detected from 425–430 nm. Measurements were acquired every second with a 0.1 second integration time.

Figure 5:
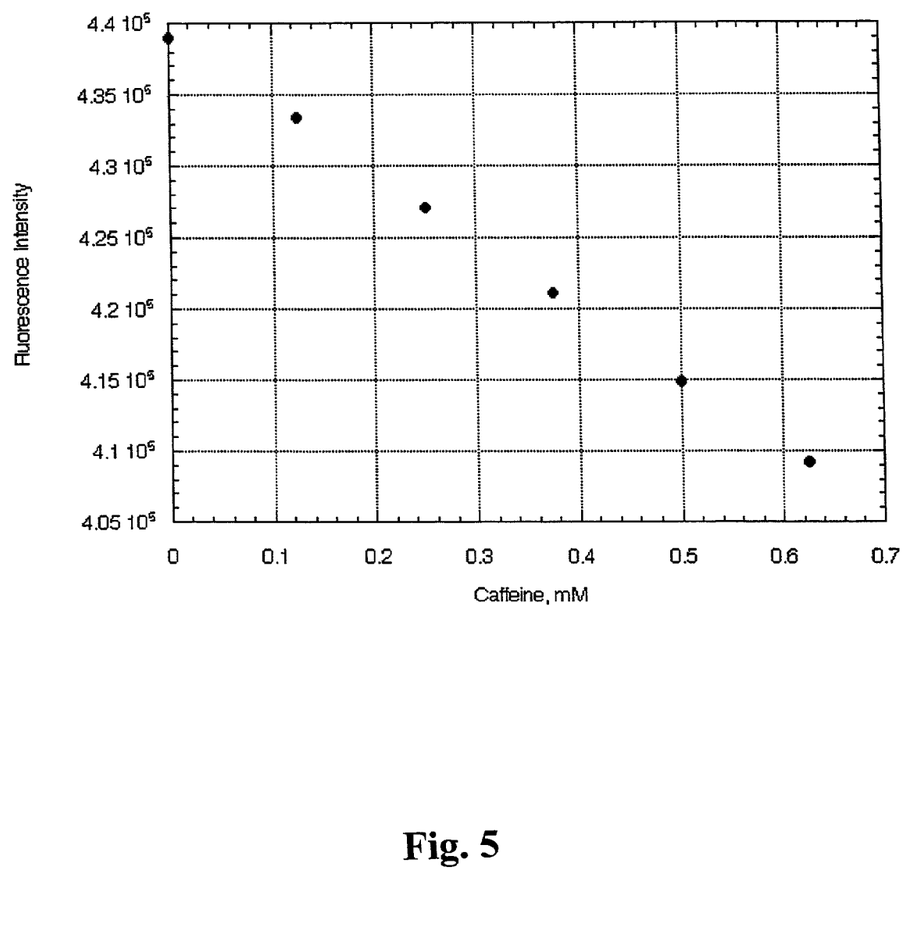
FIG. 5 is a graph of the equilibrium fluorescence intensity of vesicles in the presence of various concentrations of caffeine.

FIG. 5 shows the equilibrium fluorescence intensity of the vesicles as a function of successive additions of caffeine. The decrease in fluorescence is linear over the concentration range of caffeine. In control experiments, successive injections of equal aliquots of a test molecule into the same vesicle suspension gave identical apparent half-lives of membrane equilibration. Control experiments with the bilayer impermeable molecules, mannose and sucrose, gave no change in the fluorescence on injection.

Figure 6A:
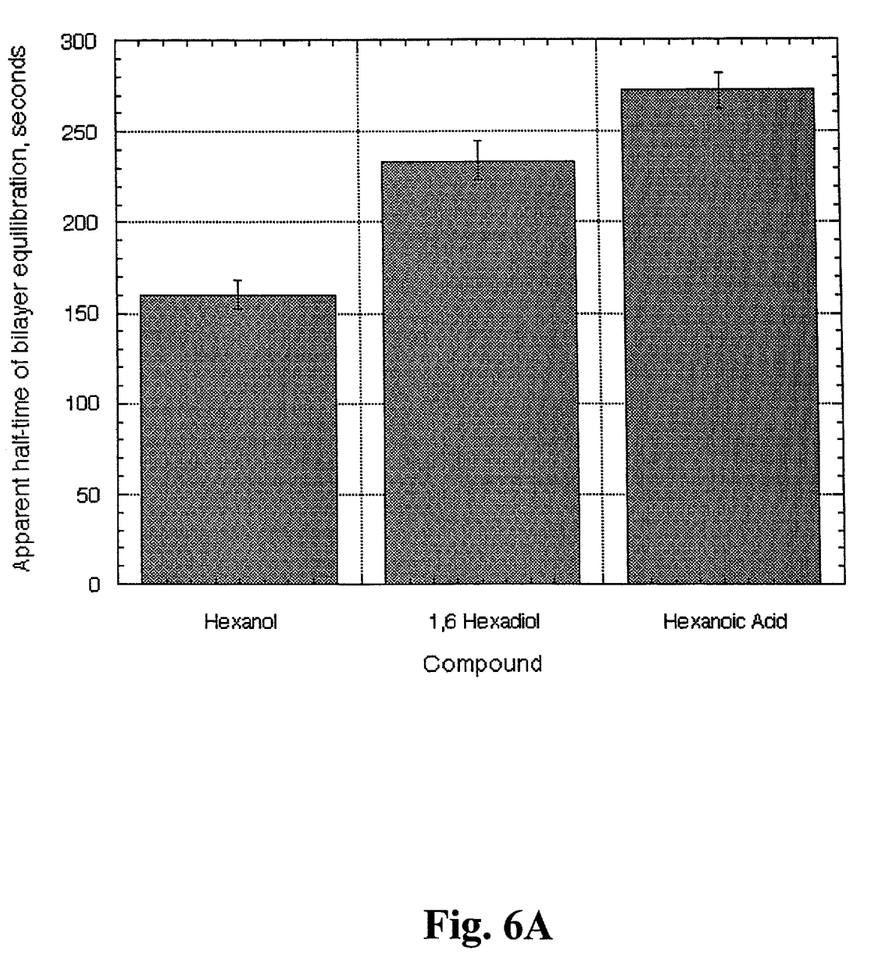
FIGS. 6A–6C are graphs showing the half-lives for bilayer entry of various compounds.
Figure 6B:
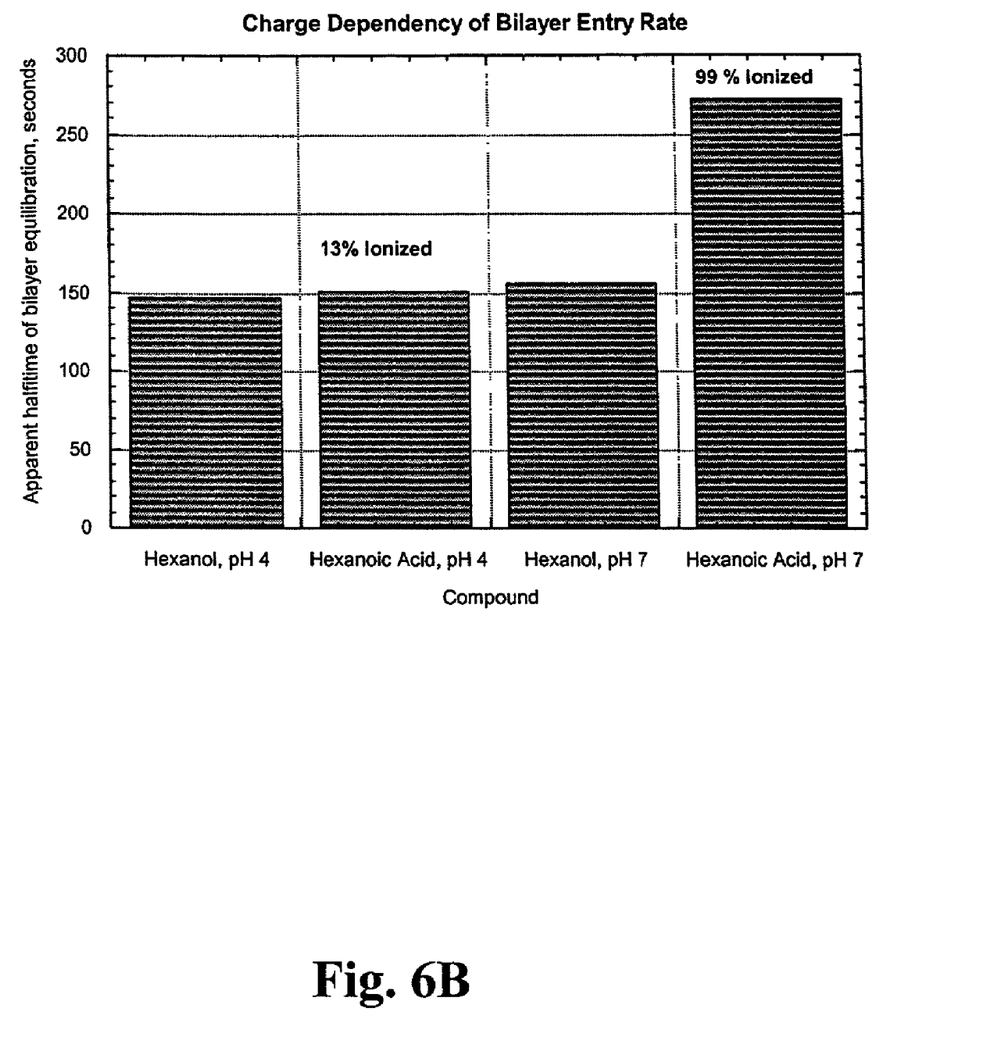
Figure 6C:
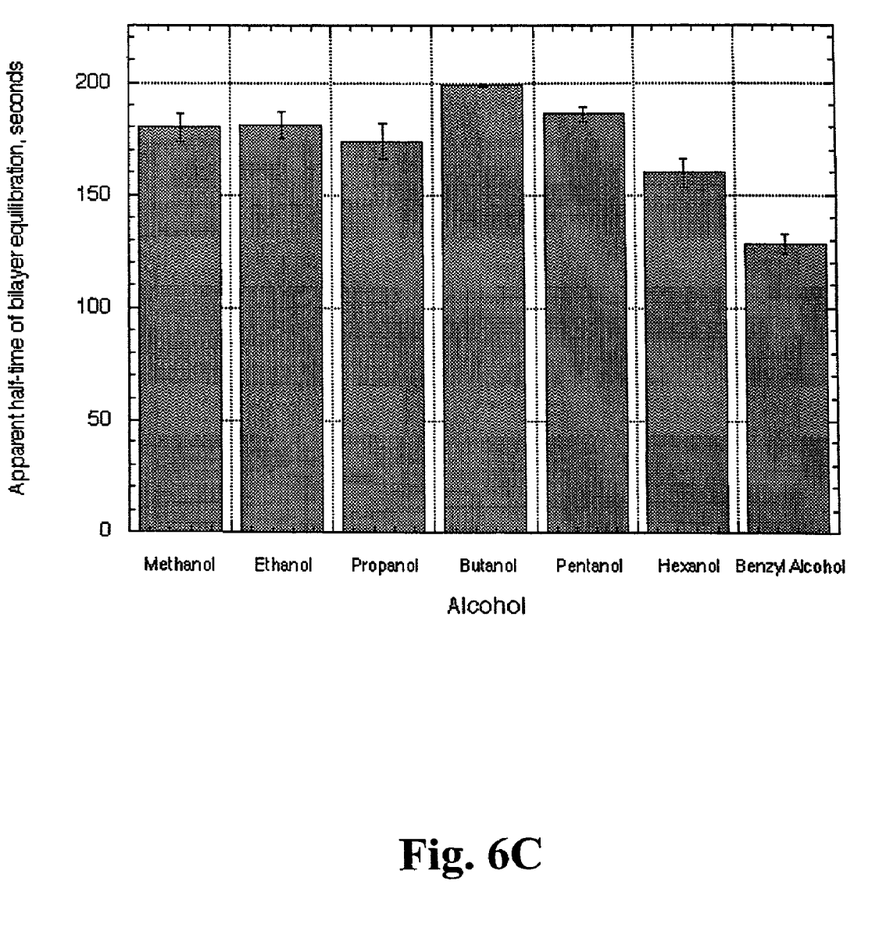

FIGS. 6A–C show the apparent half-lives of bilayer equilibration for a series of related test compounds. FIG. 6A shows the half-lives for hexanol, hexanediol, and hexanoic acid (at pH 7.0; $pK_a = 4.88$). Increasing polarity resulted in a decreased rate of membrane equilibration. FIG. 6B shows the half-lives for hexanol and hexanoic acid at pH 4.0 and 7.0. A larger percentage of the acid was ionized at pH 7.0 (>99%) than at pH 4.0 (~13%), and a concomitant increase in the half-life for bilayer entry was observed (hexanol is not substantially ionized at either pH). FIG. 6C shows the half-lives for a series of short-chain alcohols. No conclusive trend was observed, although benzyl alcohol exhibited a shorter half-life than the more polar alcohols.

Examples 6 and 7 illustrate how the methods of the invention may be used to study drug delivery vehicles or drug extraction from lipid bilayers. These assays used vesicles employing fluorophores covalently bonded to lipids and located within the interior of the bilayer. The use of bound fluorophores was desirable because a vehicle could extract an unbound fluorophore.

EXAMPLE 6

Vesicles were prepared by adding 300 µl of 26.3 mM egg phosphatidylcholine and 10.7 µl of 355 µM 2-(3-diphenylhexatrienyl)propanoyl)-1-hexadecanoyl-sn-glycero-3-phosphocholine (β-DPH-HPC, Molecular Probes, Eugene, Oreg.) together yielding a 0.05 mol % of fluorophore. The solvent was evaporated under a flow of nitrogen. The resulting film was put under vacuum (0.1 mm Hg) for 3 hours and taken up in 600 µl of 10 mM Tris buffer (pH 7.4). After 5 minutes, the suspension was agitated to form multilamellar vesicles. Unilamellar vesicles of homogenous size (100 nm±10 nm) by passing the suspension through a polycarbonate membrane (100-nm pores) 31 times (LIPO-FAST® Extrusion Apparatus, Avestin). To avoid bleaching, all preparation steps were carried out under aluminum foil. Suspensions were stored at 277 K.

Sonicated small unilamellar vesicles (sSUV) were prepared by adding 300 µl of 26.3 mM egg phosphatidylcholine in chloroform into a 6 ml flat bottom glass tube, evaporating the solvent under a nitrogen flow, and placing the resulting film under vacuum (0.1 mm Hg) for 3 hours. The resulting film was hydrated with 10 mM Tris buffer (pH 7.4) for 5 minutes and agitated to form multilamellar vesicles. 500 µl of the multilamellar vesicle suspension was transferred to a 6 ml glass tube, placed in ice water to prevent overheating, and sonicated using a sonicator microtip (Sonic Dismembrator model 300, Fisher Scientific, Bohemia, N.Y.) at 35% full power for 25 minutes until a clear sSUV solution was obtained. To avoid membrane fusion, the sSUV were stored at 277 K and used within 1 day.

Figure 7:
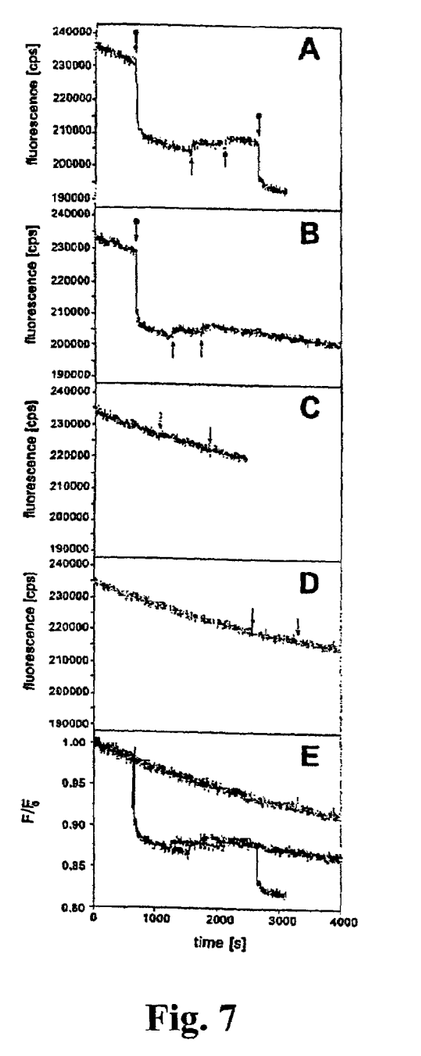
FIGS. 7A–7E are graphs of changes in fluorescence caused by phloretin entry into and extraction from a bilayer.

FIG. 7A–E show the results of interaction of phloretin with vesicles containing β-DHP-HPC and the ability of sSUV to extract the phloretin from the membrane. The baseline fluorescence intensity decreased during the experiment because of photobleaching. In FIG. 7A and B, circle-ended arrows indicate the addition of 0.5 µl of a DMSO solution of 10 mM phloretin (5 nmol added). These additions resulted in rapid and large decreases in fluorescence intensity. Sequential additions of sSUV to the suspension (regular arrows) after the addition of phloretin resulted in an increase in fluorescence as the phloretin was extracted from the vesicle bilayer. FIG. 7C and D show that addition of sSUV (C) and DMSO (D) in the absence of phloretin do not alter the fluorescence. FIG. 7E shows a normalized composite graph of FIGS. 7A–D.

EXAMPLE 7

Vesicles were prepared by adding 300 µl egg phosphatidylcholine and 20 µl of 1.7 mM 2-(6-(7-nitrobenz-2-oxa-1, 3-diazol-4-yl)amino)hexanoyl-1-hexadecanoyl-sn-glycero-3-phosphocholine (NBD-$C_6$-HPC) (0.43 mol % fluorophore) in chloroform to a glass tube. The solvent was evaporated as in Example 6. The film was taken up in 600 µl of ultrapure water (pH 5.6, 18.2 MΩ·cm, Photronix, Medway, Mass.). Unilamellar vesicles were formed like the β-DPH-HPC vesicles in Example 6.

β-estradiol loaded β-cyclodextrin (β-CD) was prepared by mixing 300 µl of 13.3 mM β-CD solution in ultrapure water with 20 µl of 40 mM β-estradiol in DMSO and 200 µl of DMSO. The solution was stirred overnight.

Figure 8:
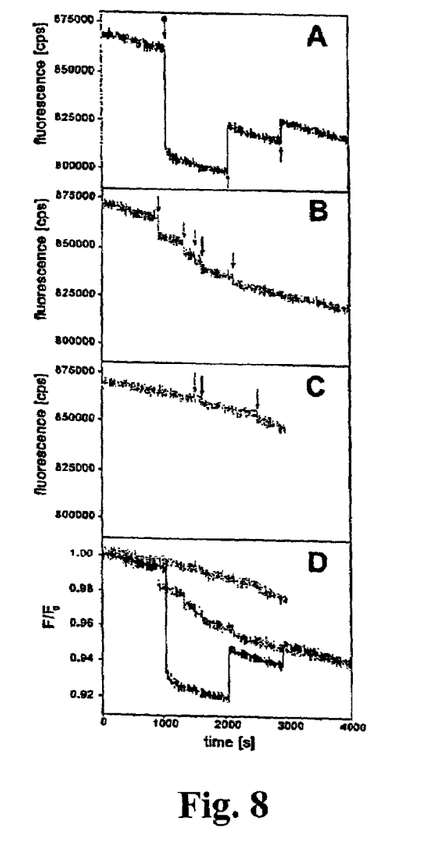
FIGS. 8A–8D are graphs of changes in fluorescence caused by β-estradiol entry into and extraction from a bilayer.

FIG. 8A–D show the results of interactions of NBD-$C_6$-HPC vesicles with β-estradiol and/or β-CD. The baseline decreased during each experiment because of photobleaching. In FIG. 8A, the circle-ended arrow indicates the addition of 1 µl of 40 mM of β-estradiol in DMSO to the vesicle suspension. Fluorescence decreased upon addition of the β-estradiol. The addition of 5 µl of 10 mM β-CD in water (regular arrows) resulted in an increase in fluorescence caused by extraction of the β-estradiol from the vesicles. In FIG. 8B, β-estradiol preincubated with β-CD was added in aliquots (arrows) to a final concentration of 40 nmol. Each addition resulted in a reduction in fluorescence. In FIG. 8C, the addition of β-CD alone did not alter the fluorescence intensity. FIG. 8D shows a normalized composite graph of FIG. 8A–C. Fluorescence measurements were made using 465 nm excitation light and detection at 538 nm.

Other Embodiments

Modifications and variations of the described methods of the invention will be apparent to those skilled in the art without departing from the scope and spirit of the invention. Although the invention has been described in connection with specific desirable embodiments, it should be understood that the invention as claimed should not be unduly limited to such specific embodiments. Indeed, various modifications of the described modes for carrying out the invention, which are obvious to those skilled in the art, are intended to be within the scope of the invention.

All publications, patents, and patent applications mentioned in this specification are hereby incorporated by reference to the same extent as if each individual publication, patent, or patent application was specifically and individually to be incorporated by reference.

Other embodiments are within the claims.

The invention claimed is:

1. A vesicle comprising:
   (a) a lipid bilayer enclosing an aqueous interior; and
   (b) a fluorescent molecule comprising a fluorophore covalently bound to a water-soluble or water-suspendable carrier, wherein said fluorescent molecule is disposed in the aqueous interior enclosed by said lipid bilayer of said vesicle,
   wherein said carrier prevents said fluorophore from traversing said lipid bilayer and wherein said vesicle is not a biological cell.

2. The vesicle of claim 1, wherein said fluorophore is selected from the group consisting of 1,6-diphenylhexa-1,3,5-triene, nitrobenzene-2-oxa-1,3-diazole, tryptophan, tyrosine, dansyl chloride, pyrene, naphthalene, and fluorescein.

3. The vesicle of claim 1, wherein said carrier is selected from the group consisting of a protein, a polypeptide, a sugar, a synthetic polymer, and a natural polymer.

4. The vesicle of claim 1, wherein said carrier comprises a serum albumin or a serum lipoprotein.

5. The vesicle of claim 1, wherein said bilayer comprises at least one of a phospholipid, sphingolipid, or glycolipid.

6. The vesicle of claim 5, wherein said lipid bilayer comprises a phosphatidylcholine.

7. The vesicle of claim 1, wherein said lipid bilayer comprises cholesterol.

8. The vesicle of claim 1, wherein said lipid bilayer comprises a protein.

9. The vesicle of claim 1, wherein said lipid bilayer comprises an isolated cell membrane.

10. The vesicle of claim 9, wherein said cell membrane is a bacterial, protozoan, animal, plant, fungal, or mycoplasma cell membrane.

11. The vesicle of claim 10, wherein said cell membrane is a mammalian cell membrane.

12. The vesicle of claim 11, wherein said mammalian cell membrane is an intestinal endothelial cell membrane.

13. The vesicle of claim 1, wherein said lipid bilayer comprises a pump.

14. The vesicle of claim 13, wherein said lipid bilayer comprises an efflux pump.

15. The vesicle of claim 1, wherein said lipid bilayer comprises a P-glycoprotein.

16. The vesicle of claim 1, wherein said fluorophore is a fluorescent monomer in a natural polymer.

17. The vesicle of claim 1, wherein said fluorophore is a fluorescent monomer in a synthetic polymer.

18. The vesicle of claim 1, wherein said lipid bilayer comprises a phosphoglyceride, ether lipid, sterol, steroid, hopanoid, carotenoid, or terpenoid.

19. The vesicle of claim 1, further comprising a protein, polypeptide, sugar, nucleic acid, synthetic or naturally occurring polymer, fatty acid, aromatic compound, alcohol, or glycol in the aqueous interior.

20. The vesicle of claim 1, wherein said carrier comprises a protein, polypeptide, poly(ethylene glycol), poly(ethylene oxide), starch, cyclodextrin polymer, a water-soluble cellulose, nucleic acid, or carbohydrate.

21. The vesicle of claim 1, wherein said vesicle has a diameter of between 25 and 10,000 nm.

22. The vesicle of claim 21, wherein said vesicle has a diameter of between 25 and 1000 nm.

23. The vesicle of claim 21, wherein said vesicle has a diameter between 100 and 300 nm.

* * * * *